United States Patent
Byrne et al.

(10) Patent No.: US 6,734,956 B2
(45) Date of Patent: May 11, 2004

(54) OPTICAL CONFIGURATION AND METHOD FOR DIFFERENTIAL REFRACTIVE INDEX MEASUREMENTS

(75) Inventors: Michael J. Byrne, East Aurora, NY (US); Keshav D. Sharma, Lancaster, NY (US); Robert C. Atkinson, Buffalo, NY (US); Bruce R. Cordier, West Seneca, NY (US)

(73) Assignee: Reichert, Inc., Depew, NY (US)

( * ) Notice: Subject to any disclaimer, the term of this patent is extended or adjusted under 35 U.S.C. 154(b) by 8 days.

(21) Appl. No.: 10/139,577

(22) Filed: May 6, 2002

(65) Prior Publication Data

US 2003/0206290 A1 Nov. 6, 2003

(51) Int. Cl.[7] .............................................. G01N 21/41
(52) U.S. Cl. ....................................... 356/128; 356/135
(58) Field of Search ......................... 356/436, 445–448, 356/128–136

(56) References Cited

U.S. PATENT DOCUMENTS

| | | |
|---|---|---|
| 4,640,616 A | 2/1987 | Michalik |
| 5,157,454 A | 10/1992 | Oka et al. |
| 5,313,264 A * | 5/1994 | Ivarsson et al. ............... 356/73 |
| 5,374,563 A | 12/1994 | Maule |
| 5,485,277 A * | 1/1996 | Foster ......................... 356/445 |
| 5,991,048 A * | 11/1999 | Karlson et al. ............. 356/445 |
| 6,172,746 B1 | 1/2001 | Byrne et al. |
| 6,268,125 B1 * | 7/2001 | Perkins .......................... 435/5 |
| 6,396,576 B1 * | 5/2002 | Bleyle .......................... 356/128 |
| 6,441,906 B2 * | 8/2002 | Dickopf et al. ............. 356/445 |
| 6,462,809 B1 * | 10/2002 | Ryan et al. .................. 356/128 |

FOREIGN PATENT DOCUMENTS

EP 0863395 A2 9/1998

* cited by examiner

Primary Examiner—Michael P. Stafira
(74) Attorney, Agent, or Firm—Hodgson Russ LLP

(57) ABSTRACT

An optical configuration for measuring a difference in refractive index between a first sample and a second sample comprises partitioned first and second optical interfaces symmetrically illuminated by an illumination beam to provide first and second partial beams defined by the refractive index of the first and second samples, respectively. A linear scanned array is aligned in a meridional plane of the optical configuration for detection purposes, and an optical multiplexor is provided upstream of the linear scanned array for receiving the first and second partial beams and defining first and second optical channels carrying optical signal information corresponding to the first and second partial beams. The optical multiplexor switches between optical channels, such that the linear scanned array detects either the first or second optical channel at a given time. Thus, differential measurements are possible using a single linear array. Embodiments for critical angle and surface plasmon resonance refractive index measurements are disclosed. The disclosure also relates to methods for measuring a difference in refractive index between a first sample and a second sample in accordance with the described optical configuration embodiments.

35 Claims, 4 Drawing Sheets

OPTICAL CONFIGURATION AND METHOD FOR DIFFERENTIAL REFRACTIVE INDEX MEASUREMENTS

FIELD OF THE INVENTION

The present invention relates generally to optical instruments for measuring refractive index of a substance, and more particularly to an optical configuration for measuring a difference in refractive index between first and second samples, for instance a test sample and a reference sample. The present invention is applicable to differential refractometers and surface plasmon resonance (SPR) biosensor devices.

BACKGROUND OF THE INVENTION

Refractometers measure the critical angle of total reflection by directing an obliquely incident non-collimated beam of light at a surface-to-surface boundary between a high refractive index prism and a sample to allow a portion of the light to be observed after interaction at the boundary. In transmitted light refractometers, light that is transmitted through the sample and prism is observed, while in reflected light refractometers, the light that is reflected due to total reflection at the surface-to-surface boundary is observed. In either case, an illuminated region is produced over a portion of a detection field of view, and the location of the shadowline between the illuminated region and an adjacent dark region in the detection field of view allows the sample refractive index to be deduced geometrically. Differential refractometers, for example that disclosed in U.S. Pat. No. 5,157,454, have been developed for measuring a difference in refractive index between a test sample and a known reference sample, whereby variable test conditions effecting the measurement result, such as sample temperature, illumination level, etc., can be "subtracted out" to yield a more accurate and precise measurement result. The prior art differential refractometers known to applicants involve moving parts which malfunction or wear out over time, and/or are restricted to the transmitted light variety so as to prevent measurement of samples having relatively high opacity.

Optical biosensor devices designed to analyze binding of analyte molecules to a binding layer by observing changes in internal reflection at a sensing interface are also part of the related prior art. More specifically, U.S. Pat. No. 5,313,264 to Ivarsson et al. describes an optical biosensor system that comprises a plurality of side-by-side sensing surfaces 39A–D illuminated by a streak of light 5 extending transversely across the sensing surfaces, and an anamorphic lens system 6 by which rays of light reflected from the respective sensing surfaces are imaged on corresponding columns of a two-dimensional array 7 of photosensitive elements. Accordingly, the signals from the photosensitive elements can be processed to determine a minimum reflectance associated with the resonance angle at each sensing surface. Although the system described in U.S. Pat. No. 5,313,264 avoids the use of moving parts, it is nevertheless optically complex and requires a two-dimensional array, factors that are accompanied by an increase in cost.

Finally, it is noted that one-dimensional (linear) arrays of photosensitive elements cells are commonly used in automatic refractometers designed to take non-differential readings with respect to a single test sample. Examples can be found in U.S. Pat. No. 4,640,616 (Michalik) and U.S. Pat. No. 6,172,746 (Byrne et al.). However, applicants are unaware of any critical angle optical device for differential refractive index measurements that operates using a linear array, despite the recognized economy offered by this type of array.

BRIEF SUMMARY OF THE INVENTION

Therefore, it is an object of the present invention to provide an optical configuration for differential refractive index measurements wherein a first sample and a second sample are illuminated by a single illuminating beam.

It is another object of the present invention to provide an optical configuration for differential refractive index measurements that does not rely on moving parts.

It is a further object of the present invention to provide an optical configuration for differential refractive index measurements wherein detected light has been reflected rather than transmitted at an optical interface of the configuration.

It is a further object of the present invention to provide an optical configuration for critical angle differential refractive index measurements wherein light interacting at first and second optical interfaces corresponding to a first sample and a second sample is detected by a single linear scanned array of photoelectric cells.

It is a further object of the present invention to provide an optical configuration for differential refractive index measurements in accordance with the objects stated above, and which operates based on surface plasmon resonance principles for use in a biosensor device.

An optical configuration formed in accordance with a first embodiment of the present invention comprises an optical path defining a meridional plane of the configuration. A high index prism in the optical path includes a sample surface divided by a partition residing in the meridional plane, such that a first sample and a second sample supported by the sample surface are located on opposite sides of the meridional plane to establish a first optical interface associated with the first sample and a second optical interface associated with the second sample. An illumination beam traveling along the optical path illuminates both optical interfaces simultaneously to provide a first partial beam defined by the refractive index of the first sample and a second partial beam defined by the refractive index of the second sample. A collecting lens collimates the first and second partial beams and an optical multiplexor means receives the collimated partial beams and defines first and second optical channels containing optical signal information associated with the first and second partial beams, respectively. A cylinder lens and/or a biprism after the optical multiplexing means deflects the partial beams laterally toward the meridional plane of the system for illuminating a linear scanned array of photoelectric cells aligned in the meridional plane. In a first embodiment, the optical multiplexing means comprises a liquid crystal shutter programmed to alternately transmit one partial beam while blocking the other partial beam such that a given scan of the linear array provides signal information with respect to either the first partial beam or the second partial beam, depending upon the corresponding state of the liquid crystal shutter. In a second embodiment, a similar arrangement is used, however the liquid crystal shutter is programmed to transmit and block predetermined portions of each partial beam in an alternating fashion, such that for a given scan of the linear array some of the array cells will provide signal information relating to the first partial beam and some of the cells will provide signal information relating to the second partial beam. The first partial beam exhibits a feature, such as a shadowline or resonance minimum, on the linear scanned array the location of which is indicative of the refractive index of the first sample, while the second partial beam exhibits a similar feature the location of which is indicative of the refractive index of the second sample.

A third embodiment based on the first and second embodiments is an adaptation of the basic configuration in order to observe molecular interactions, particularly specific binding of analyte molecules to a binding layer, using the principles of surface plasmon resonance. In accordance with the third embodiment, a thin metallic film is applied to a slide placed on the sample surface or directly to the sample surface, and the first sample and second sample are brought into contact with the metallic film to define first and second evanescent wave optical interfaces. In this embodiment, the locations of resonance minimums exhibited by the first and second partial beams are detected.

The present invention further encompasses methods for measuring a difference in refractive index between a first sample and a second sample based on the specified optical configurations.

BRIEF DESCRIPTION OF THE SEVERAL VIEWS OF THE DRAWINGS

The nature and mode of operation of the present invention will now be more fully described in the following detailed description of the invention taken with the accompanying drawing figures, in which.

DETAILED DESCRIPTION OF THE INVENTION

Figure 1:
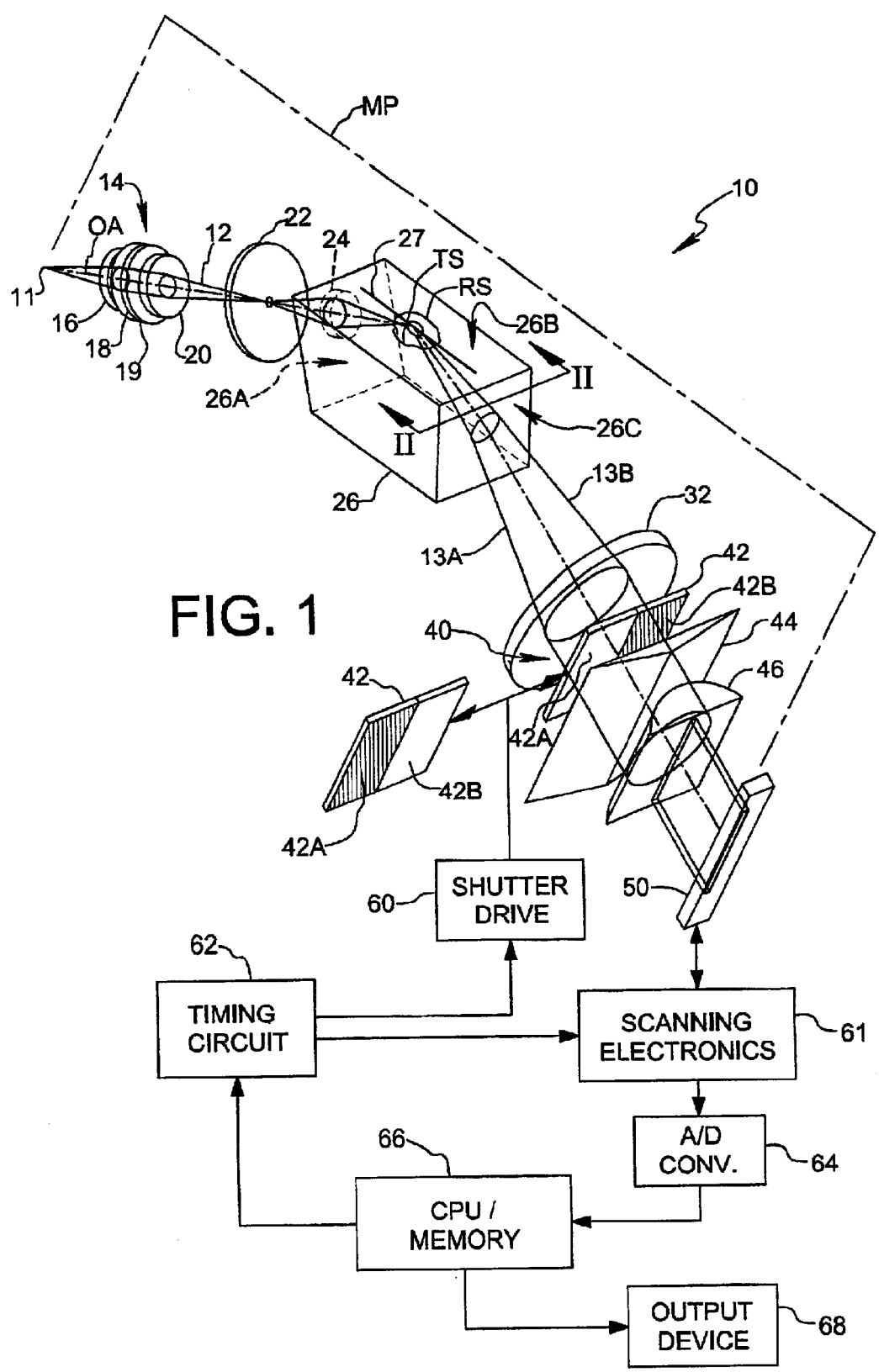
FIG. 1 is a perspective schematic view of an optical configuration formed in accordance with a first embodiment of the present invention.

An optical configuration formed in accordance with a first embodiment of the present invention will now be described with reference to FIG. 1 of the drawings. The optical configuration of the first embodiment is shown generally at FIG. 1 and is designated by the reference numeral 10. Optical configuration 10 includes an illumination beam 12 traveling along an optical path OP from the beam's origin at a light source 11. Illumination beam 12 travels through a focusing optical system 14 preferably including a collimating lens 16, a narrow bandpass filter 18 for transmitting a narrow bandwidth of light having a central wavelength of 589 nm, a linear polarizer 19, and a focusing lens 20. The convergent illumination beam then passes through a pinhole stop 22 at the focal plane of focusing optical system 14. The divergent beam 12 is then re-focused by a lens 24 and enters a high refractive index prism 26, for example a sapphire prism, that includes a light entry surface 26A, a sample surface 26B contacted by test sample TS and reference sample RS, and a light exit surface 26C. Preferably, lens 24 is affixed with optical cement to light entry surface 26A of prism 26. The illuminating light is focused at a point within prism 26 just below sample surface 26B, after which point the beam once again becomes divergent. It is noted that polarizer 19 is provided to enable use of the optical configuration in connection with surface plasmon resonance measurements as will be described in a subsequent portion of this description that makes reference to FIGS. 4 and 5.

Illumination beam 12 approaches sample surface 26B as a beam of non-parallel light rays, in this instance divergent light rays, which are obliquely incident to sample surface 26B at various angles of incidence within a range of angles. Sample surface 26B is divided by a partition 27 into a first area for receiving a test sample TS and a second area for receiving a reference sample RS. Partition 27 is coplanar with optical path OP as the optical path approaches sample surface 26B such that the light rays making up illumination beam 12 are symmetrically apportioned between a first optical interface 30A associated with the test sample TS and a second optical interface 30B associated with the reference sample RS. Partition 27 is chosen to provide a fluid seal between test sample TS and reference sample RS to prevent the samples from mixing. A synthetic rubber gasket material, for example room temperature vulcanizing (RTV) silicon rubber or VITON® synthetic rubber composition, will provide a suitable barrier.

In the present embodiment, first optical interface 30A and second optical interface 30B are critical angle optical interfaces respectively defined by the contact area of test sample TS with sample surface 26B and by the contact area of reference sample RS with sample surface 26B. These contact areas can be established by dropping the test sample TS and reference sample RS onto sample surface 26B on opposite sides of partition 27, by using a flow cell designed to bring test sample TS and reference sample RS into contact with sample surface 26B on opposite sides of partition 27, or by otherwise applying test sample TS and reference sample RS to the respective areas of sample surface 26B. The portion of illumination beam 12 reaching first optical interface 30A will interact at such interface in accordance with Snell's Law, whereby rays incident at an angle greater than or equal to the critical angle will be totally internally reflected from sample surface 26B, and rays incident at an angle less than the critical angle will be refracted and transmitted through the test sample and out of the optical system. Accordingly, the internally reflected light forms a first partial beam 13A that is defined by the index of refraction of test sample TS. A similar interaction occurs for the portion of illumination beam 12 reaching second optical interface 30B, whereby internally reflected light forms a second partial beam 13B that is defined by the index of refraction of reference sample RS. First partial beam 13A and second partial beam 13B then pass through exit surface 26C and continue through a collecting lens 32 for converting the divergent light rays to parallel light rays.

In accordance with the present invention, an optical multiplexing means designated generally as 40 is positioned in optical path OP after collecting lens 32 to receive first partial beam 13A and second partial beam 13B. Optical multiplexing means 40 defines a first optical channel containing optical signal information associated with first partial beam 13A and a second optical channel containing optical signal information associated with second partial beam 13B. In the embodiment of FIG. 1, optical multiplexing means 40 comprises an electro-optical shutter 42 having a first area 42A arranged to receive first partial beam 13A and a second area 42B arranged to receive second partial beam 42B. In a preferred arrangement, shutter 42 is centered with respect to optical axis OP, and first and second areas 42A and 42B are halves of the shutter on opposite sides of meridional plane MP.

As seen in FIG. 1, shutter 42 is connected to a shutter drive circuit 60 that signals shutter 42 to alternate at a predetermined frequency between a condition wherein first area 42A is transparent and second area 42B is opaque, and a condition wherein first area 42A is opaque and second area 42B is transparent. As a result, optical multiplexing means 40 defines a first optical channel corresponding to the exclusive transmission of first partial beam 13A and a second optical channel corresponding to the exclusive transmission of second partial beam 13B. It will be readily apparent to those skilled in the art that optical multiplexing means 40 can comprise two individual optical shutters respectively allocated to first partial beam 13A and second partial beam 13B and driven in opposite synchronization to produce the desired definition of optical channels. Electro-optical shutter 42 may be a commercially available liquid crystal shutter. Other types of optical shutters may also be used, including mechanical choppers and shutters, acousto-optical shutters, and magnetic shutters.

A biprism 44 and a cylindrical lens 46 are positioned along optical path OP downstream of optical multiplexing means 40 for redirecting partial beams 13A and 13B laterally toward meridional plane MP. Biprism 44 and cylinder lens 46 act as an anamorphic system to cause each partial beam to be imaged as a line of light illuminating photoelectric cells of a linear scanned array 50 aligned in meridional plane MP. Depending upon the geometry of optical configuration 10, it is contemplated to provide only one anamorphic optical element, for example either biprism 44 or cylinder lens 46, to achieve a line of light at linear scanned array 50, as this would save the cost of providing and locating an additional optical element.

Linear scanned array 50 receives first partial beam 13A and second partial beam 13B in alternating succession, such that optical signal information associated with either the first optical channel or the second optical channel is transmitted to and received by the linear scanned array at any given instant in time. The timing and frequency at which scanning electronics 61 scans linear array 50 is synchronized by a timing circuit 62 with the oscillation of multiplexing means 40 between the first and second optical channels, whereby a particular optical channel (first or second) is attributable to each scan of linear array 50. The signal information provided by linear scanned array 50 is preferably summed over a plurality of scans for each respective optical channel. For example, the frequency at which electro-optical shutter 42 alternates between transmission of the first and second optical channels can be less than the scanning frequency of said linear scanned array to allow signal information from a particular optical channel to be accumulated before switching to the other optical channel.

As is well understood in the art of critical angle refractometry, first partial beam 13A will exhibit a shadowline at a first location on linear scanned array 50 that is indicative of the refractive index of test sample TS. In similar fashion, second partial beam 13B will exhibit a shadowline on linear scanned array 50 that is indicative of the refractive index of reference sample RS. For example, when test sample TS and reference sample RS have the same index of refraction, their respective shadowlines will appear at the same cell-crossing location on linear scanned array 50. Consequently, the difference in cell-crossing location between the test sample and reference sample shadowlines on linear scanned array 50 provides an indication of the difference in refractive index between the test sample and reference sample. If the refractive index of the reference sample RS is known for the particular test conditions, the refractive index of the test sample TS can be calculated from the measured difference in shadowline locations.

It is noted here that various algorithms are available for determining shadowline location on a linear scanned array, as taught for example by U.S. Pat. Nos. 4,640,616; 5,617,201; and 6,172,746; and by commonly-owned U.S. patent application Ser. No. 09/794,991 filed Feb. 27, 2001, each of these documents being hereby incorporated by reference in the present specification. The analog pulse signals from the cells of linear scanned array 50 are digitized by an analog-to-digital converter 64, and the digitized array information is processed by a central processing unit 66. An output device 68, such as a liquid crystal display, computer monitor, printer, or the like, is connected to central processing unit 66 for reporting computed measurement results.

Figure 2:
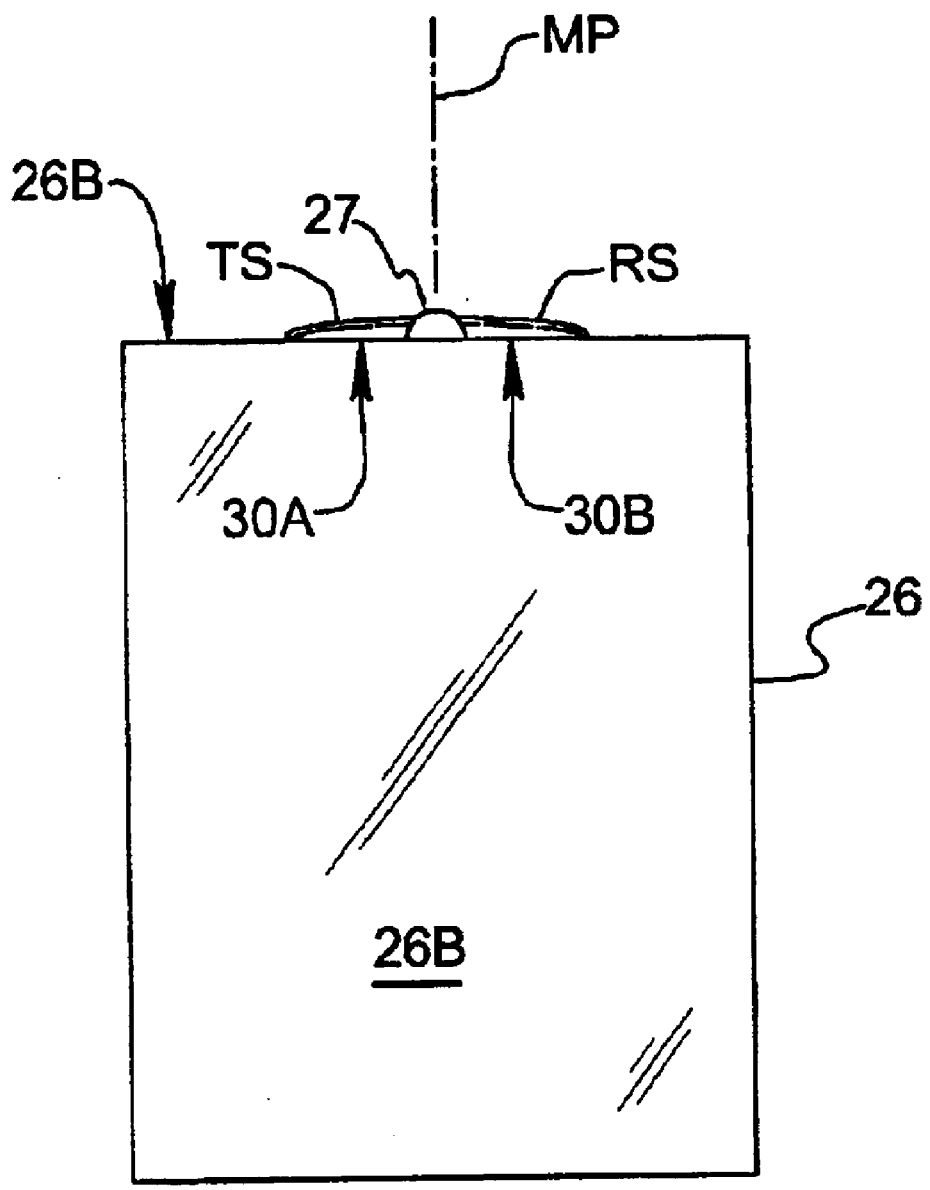
FIG. 2 is a view taken generally along the line 11—11 in FIG. 1.

FIG. 2 illustrates an optical configuration formed in accordance with a second embodiment of the present invention and identified by reference numeral 110. Optical configuration 110 is similar to optical configuration 10 of the first embodiment, with electro-optical shutter 42 having a first area 42A for receiving a first partial beam 13A and a second area 42B for receiving second partial beam 13B. However, in the second embodiment, each of the first and second areas is subdivided into a plurality of sub areas 52A and 52B, respectively. The sub-areas 52A provide a grid-like pattern of opaque and transparent regions in first area 42A, while the sub-areas 52B provide a corresponding but opposite grid of opaque and transparent regions in second area 42B. The various sub-areas 52A, 52B of electro-optical shutter 42 are alternated at a predetermined frequency between opaque and transparent states. As a consequence, each scan of linear scanned array 50 will extract signal information from both the first and second optical channels, but at half the resolution of a single channel scan according to the first embodiment. Thus, in the embodiment of FIG. 2, the first optical channel is defined by pulsed transmission of interlaced portions of the first partial beam in alternating succession, and said second optical channel is defined by pulsed transmission of interlaced portions of said second partial beam in alternating succession.

Figure 3:
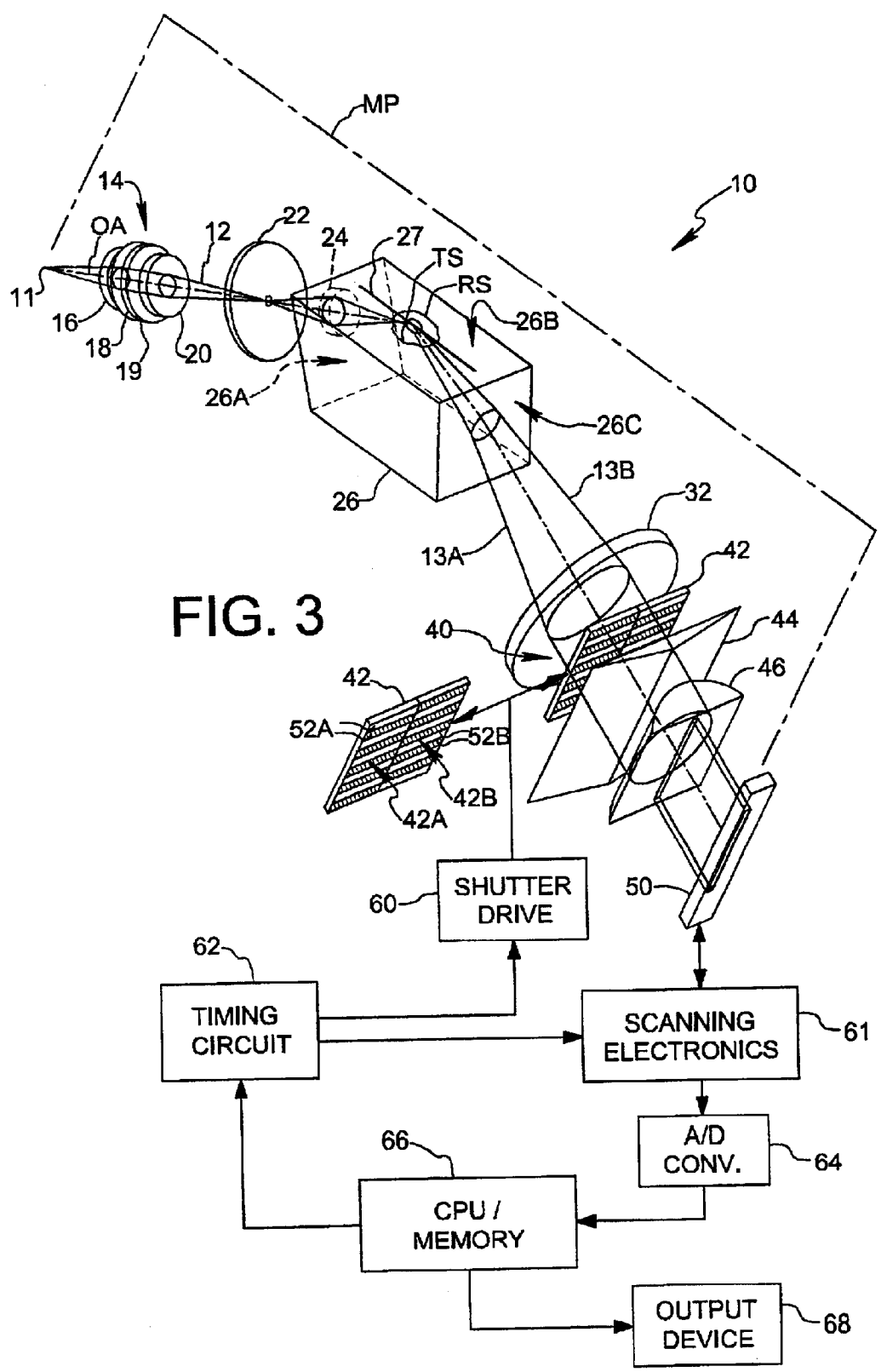
FIG. 3 is a view similar to that of FIG. 1, however showing an optical configuration formed in accordance with a second embodiment of the present invention.

It will be recognized that the basic optical arrangements of FIG. 1 or 3 can be used in connection with evanescent wave optical interfaces rather than critical angle optical interfaces by coupling a glass slide having a thin metallic film to sample surface 26B, or by directly coating sample surface 26B with a thin metallic film. In the arrangement shown in FIG. 4, a glass slide 70 is provided with a thin metallic film 72 on an upwardly facing surface thereof. In the present embodiment, metallic film 72 includes a layer of chromium approximately ten angstroms thick for adherence to the glass surface of slide 70, and a gold layer approximately fifty nanometers thick. A synthetic rubber material, such as RTV silicon, VITON® synthetic rubber composition, or like material is applied to metallic film 72 to provide partition 27. Metallic film 72 is optically coupled, indirectly, to prism sample surface 26B through transparent glass slide 70 and a thin layer of transparent oil 74 provided between the underside of glass slide 70 and sample surface 26B. Of course, metallic film 72 can be optically coupled to sample surface 26B by applying the film directly to sample surface 26B, as illustrated in FIG. 5. Test sample TS and reference sample RS are contacted with metallic coating 72 on opposite sides of partition 27, such that respective first and second optical interfaces are established. As light from illumination beam 12 reaches metallic film 72 at the first optical interface, certain rays will be incident at a resonance angle determined by the refractive index of test sample TS and energy associated with such rays will be absorbed, while the remainder of the rays will be internally reflected by metallic film 72. As a result of surface plasmon resonance, first partial beam 13A exhibits a resonance minimum at a first location on linear scanned array 50 that is indicative of the refractive index of test sample TS. Likewise, second partial beam 13B will exhibit a resonance minimum at a second location on linear scanned array 50 that is indicative of the refractive index of reference sample RS. It is noted here that for surface plasmon resonance applications, a narrow band-pass filter 18 preferably transmits light having a central wavelength of 780 nm.

Figure 4:
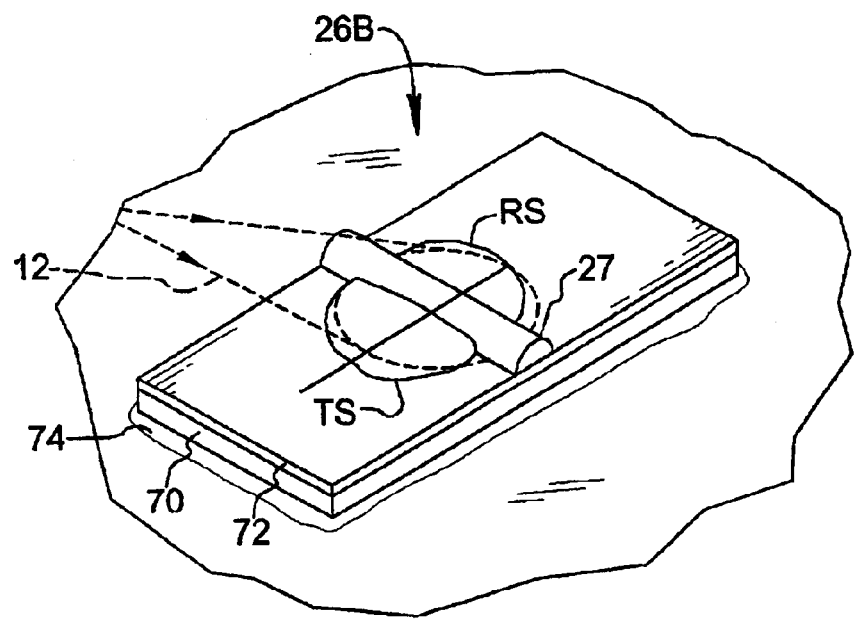
FIG. 4 is a perspective view showing an optical interface portion of an optical configuration formed in accordance with a third embodiment of the present invention relating to surface plasmon resonance.
Figure 5:
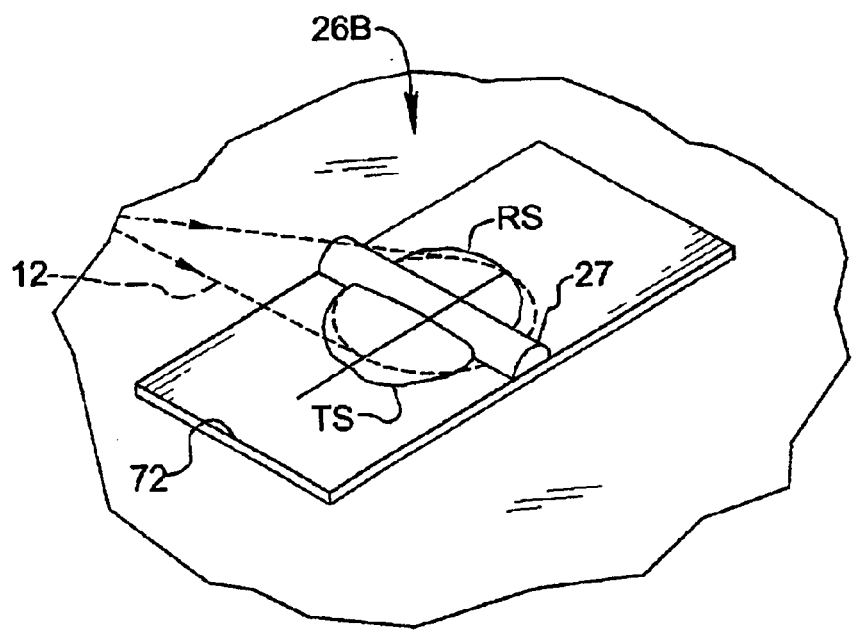
FIG. 5 is a perspective view showing an optical interface portion of an optical configuration formed in accordance with a fourth embodiment of the present invention also relating to surface plasmon resonance.

The embodiments of FIGS. 3 and 4 based on evanescent wave principles find useful application in the observation of molecular interactions, particularly in the analysis of specific binding of analyte molecules to a binding layer. Accordingly, prepared slides having a predetermined, application-specific binding layer applied to metallic film 72 can be produced for use with a variety of analytes.

What is claimed is:

1. An optical configuration for use in measuring a difference in refractive index between a first sample and a second sample, said optical configuration comprising:
   a first optical interface associated with said first sample;
   a second optical interface associated with said second sample;
   an illumination beam traveling along an optical path, light from said illumination beam being incident upon said first and second optical interfaces to provide a first partial beam defined by the refractive index of said first sample and a second partial beam defined by the refractive index of said second sample;
   a linear scanned array comprising a plurality of photoelectric cells each providing an output pulse during a scan having an amplitude determined by the amount of illumination of the corresponding cell by incident light; and
   optical multiplexing means upstream of said linear scanned array for receiving said first and second partial beams and defining first and second optical channels, said first optical channel containing optical signal information associated with said first partial beam and said second optical channel containing optical signal information associated with said second partial beam, said first partial beam exhibiting a feature indicative of said refractive index of said first sample on said array and said second partial beam exhibiting a feature indicative of said refractive index of said second sample on said array.

2. The optical configuration recited in claim 1 wherein said difference in refractive index can be determined from a difference between the respective locations of said exhibited features on said array.

3. The optical configuration according to claim 1, wherein said optical path defines a Y-Z meridional plane of said optical configuration and said first and second optical interfaces are located on opposite sides of said Y-Z meridional plane.

4. The optical configuration according to claim 3, wherein said linear scanned array is aligned in said Y-Z meridional plane.

5. The optical configuration according to claim 1, wherein said first and second optical interfaces are critical angle optical interfaces, such that said first and second partial beams exhibit respective shadowlines as features on said array.

6. The optical configuration according to claim 1, wherein said first and second optical interfaces are evanescent wave optical interfaces, such that said first and second partial beams exhibit respective resonance minimums as features on said array.

7. The optical configuration according to claim 1, wherein said optical multiplexing means comprises a liquid crystal shutter.

8. The optical configuration according to claim 7, wherein said liquid crystal shutter defines a first area arranged to receive said first partial beam and a second area arranged to receive said second partial beam, said first area of said shutter alternating between a transmitting state and an opaque state and said second area of said shutter alternating between an opaque state and a transmitting state in opposite synchronization with said first area of said shutter.

9. The optical configuration according to claim 7, wherein said liquid crystal shutter defines a first area arranged to receive said first partial beam and a second area arranged to receive said second partial beam, said first area of said shutter defining a pattern of sub-areas alternating spatially and temporally between a transmitting state and an opaque state and said second area of said shutter defining a corresponding pattern of sub-areas alternating spatially and temporally between a transmitting state and an opaque state in opposite synchronization with said pattern of sub-areas of said first area of said shutter.

10. The optical configuration according to claim 1, wherein said first and second optical interfaces are prepared on a slide selectively movable into and out of said optical path.

11. The optical configuration according to claim 4, further comprising a prism including a light entry surface, a light exit surface, and said sample surface, said illumination beam entering said prism through said light entry surface, and said first and second partial beams exiting said prism through said light exit surface.

12. The optical configuration according to claim 11, wherein said first and second optical interfaces are formed by contacting a first area of said sample surface with said first sample and contacting a second area of said sample surface with said second sample.

13. The optical configuration according to claim 12, further comprising a partition for dividing said sample surface of said prism along said Y-Z meridional plane to prevent mixing of said first sample and said second sample.

14. The optical configuration according to claim 13, wherein said partition is formed of synthetic rubber.

15. The optical configuration according to claim 11, wherein said first and second optical interfaces are formed by coupling a metal film to said sample surface, said metal film having a first area contacted by said first sample and a second area contacted by said second sample.

16. The optical configuration according to claim 15, wherein said metal film is indirectly coupled to said sample surface.

17. The optical configuration according to claim 15, wherein said metal film is directly coupled to said sample surface.

18. The optical configuration according to claim 11, further comprising an optical element after said optical multiplexing means for receiving said first and second partial beams and redirecting said first and second partial beams along converging directions toward said meridional plane.

19. The optical configuration according to claim 18, wherein said optical element is a cylinder lens.

20. The optical configuration according to claim 18, wherein said optical element is a biprism.

21. The optical configuration according to claim 11, further comprising a focusing lens for focusing said illumination beam at a point within said prism, whereby said beam of light becomes a diverging cone of light having respective symmetrical portions on opposite sides of said meridional plane to be incident upon said first and second optical interfaces.

22. The optical configuration according to claim 21, wherein said focusing lens is affixed to said light entry surface of said prism.

23. The optical configuration according to claim 1, wherein one of said first and second samples is a reference sample having a known index of refraction.

24. A method for measuring a difference in refractive index between a first sample and a second sample, said method comprising the steps of:
A) providing a transparent medium having a sample surface;
B) contacting a first area of said sample surface with said first sample and a second area of said sample surface with said second sample;
C) illuminating an interface of said transparent medium and said first sample and an interface of said transparent medium and said second sample with a beam of light having obliquely incident divergent rays to provide a first partial beam defined by the refractive index of said first sample and a second partial beam defined by the refractive index of said second sample;
D) defining first and second optical channels, said first optical channel containing optical signal information associated with said first partial beam and said second optical channel containing optical signal information associated with said second partial beam;
E) arranging a single linear scanned array of photoelectric cells to detect said optical signal information contained by said first optical channel and said optical signal information contained by said second optical channel;
F) determining a location of a first sample critical angle shadowline on said linear scanned array using said first optical channel, and a location of a second sample critical angle shadowline on said linear scanned array using said second optical channel; and
G) calculating said difference in refractive index based on a distance between said location of said first sample critical angle shadowline and said location of said second sample critical angle shadowline on said linear scanned array.

25. The method according to claim 24, wherein said step of defining first and second optical channels is performed by means of an optical multiplexor.

26. The method according to claim 25, wherein said first optical channel is defined by pulsed transmission of said first partial beam at a regular frequency, and said second optical channel is defined by pulsed transmission of said second partial beam at said regular frequency but out of timing phase with said first optical channel.

27. The method according to claim 26, wherein said optical multiplexor alternates between said first and second optical channels at a frequency that is less than the scanning frequency of said linear scanned array.

28. The method according to claim 25, wherein said first optical channel is defined by pulsed transmission of interlaced portions of said first partial beam in alternating succession, and said second optical channel is defined by pulsed transmission of interlaced portions of said second partial beam in alternating succession.

29. The method according to claim 24, wherein one of said first and second samples is a reference sample having a known index of refraction.

30. A method for measuring a difference in refractive index between a first sample and a second sample, said method comprising the steps of:
A) providing a transparent medium having a metal film adhered thereto;
B) contacting a first area of said metal film with said first sample and a second area of said metal film with said second sample;
C) illuminating an interface of said transparent medium and said metal film with a beam of light having divergent rays obliquely incident to said interface, said beam of light simultaneously irradiating said interface at a first region opposite said first area and a second region opposite said second area to provide a first partial beam defined by the refractive index of said first sample and a second partial beam defined by the refractive index of said second sample;
D) defining first and second optical channels, said first optical channel containing optical signal information associated with said first partial beam and said second optical channel containing optical signal information associated with said second partial beam;
E) arranging a single linear scanned array of photoelectric cells to detect said optical signal information contained by said first optical channel and said optical signal information contained by said second optical channel;
F) determining a location of a first resonance induced flux minimum associated with said first sample on said linear scanned array using said first optical channel, and a location of a second resonance induced flux minimum associated with said second sample on said linear scanned array using said second optical channel; and
G) calculating said difference in refractive index based on a distance between said first resonance induced flux minimum and said second resonance induced flux minimum on said linear scanned array.

31. The method according to claim 30, wherein said step of defining first and second optical channels is performed by means of an optical multiplexor.

32. The method according to claim 31, wherein said first optical channel is defined by pulsed transmission of said first partial beam at a regular frequency, and said second optical channel is defined by pulsed transmission of said second partial beam at said regular frequency but out of timing phase with said first optical channel.

33. The method according to claim 32, wherein said optical multiplexor alternates between said first and second optical channels at a frequency that is less than the scanning frequency of said linear scanned array.

34. The method according to claim 31, wherein said first optical channel is defined by pulsed transmission of interlaced portions of said first partial beam in alternating succession, and said second optical channel is defined by pulsed transmission of interlaced portions of said second partial beam in alternating succession.

35. The method according to claim 30, wherein one of said first and second samples is a reference sample having a known index of refraction.

* * * * *